United States Patent [19]

Bouhour et al.

[11] Patent Number: 6,078,836
[45] Date of Patent: Jun. 20, 2000

[54] ACTIVE IMPLANTABLE MEDICAL DEVICE FOR THE REDUCTION OF CARDIAC ARRHYTHMIAS BY MODIFYING THE ESCAPE INTERVAL AND METHODS THEREFOR

[75] Inventors: Anne Bouhour, Ville D'Avray; Marcel Limousin, Paris; Jean-Luc Bonnet, Montrouge, all of France

[73] Assignee: ELA Medical S.A., Montrouge, France

[21] Appl. No.: 09/079,333

[22] Filed: May 14, 1998

[30] Foreign Application Priority Data

May 16, 1997 [FR] France ................................. 97 06021

[51] Int. Cl.$^7$ .................................................. A61N 1/362
[52] U.S. Cl. .......................................................... 607/14
[58] Field of Search ................................. 607/9, 14, 27

[56] References Cited

U.S. PATENT DOCUMENTS

| | | | |
|---|---|---|---|
| 3,857,399 | 12/1974 | Zacouto | 607/9 |
| 3,921,642 | 11/1975 | Preston et al. | 607/9 |
| 4,421,114 | 12/1983 | Berkovits et al. | 607/14 |
| 5,284,491 | 2/1994 | Sutton et al. | |
| 5,312,451 | 5/1994 | Limousin et al. | |
| 5,480,413 | 1/1996 | Greenhut et al. | |

FOREIGN PATENT DOCUMENTS

| | | | |
|---|---|---|---|
| 0318304 | 5/1989 | European Pat. Off. | A61N 1/365 |
| 0550342 | 7/1993 | European Pat. Off. | A61N 1/368 |
| 0714676 | 6/1996 | European Pat. Off. | A61N 1/368 |
| 2061734 | 5/1981 | United Kingdom | A61N 1/36 |
| WO 95/29734 | 11/1995 | WIPO | A61N 1/365 |
| WO 97/41922 | 11/1997 | WIPO | A61N 1/368 |

*Primary Examiner*—William E. Kamm
*Attorney, Agent, or Firm*—Orrick, Herrington & Sutcliffe LLP

[57] ABSTRACT

An active implantable medical device, especially of the cardiac pacemaker, defibrillator and/or cardiovertor type, and method for the reduction of episodes of arrhythmia, and especially of atrial arrhythmias. The device operates by detecting events of spontaneous electrical activity in a cardiac cavity, especially the atrium; delivering a stimulation to the aforementioned cardiac cavity, which stimulation is controlled according to an actual escape interval such that, at each cardiac cycle, a stimulation is delivered to the cavity if no spontaneous event is detected by the end of a time corresponding to the end of the period of escape interval since the last spontaneous event or the last stimulation in the cavity; counting of the number of successive stimulated events; and discriminating between events detected in the cavity of an extrasystole origin or a non-extrasystole origin. Preferably, the escape interval is modifiable at each cardiac cycle in a manner so as to reduce by a first programmable value the actual escape interval after the detection of a event of spontaneous non extrasystole origin, or to increase by the actual escape interval a second value programmable after delivery of a predetermined number of successive stimulations.

19 Claims, 3 Drawing Sheets

ACTIVE IMPLANTABLE MEDICAL DEVICE FOR THE REDUCTION OF CARDIAC ARRHYTHMIAS BY MODIFYING THE ESCAPE INTERVAL AND METHODS THEREFOR

FIELD OF THE INVENTION

The present invention concerns "active implantable medical devices" such as those defined in the directive 90/385/EEC of Jun. 20, 1990 of the European Community Council, more particularly cardiac pacemaker, defibrillator and/or cardiovertor devices which deliver an electrical impulse of low energy (a "stimulation") to the heart for the treatment of "trouble of the cardiac rhythm".

BACKGROUND OF THE INVENTION

The following discussion concerns mainly the processing of trouble of the atrial rhythm with such devices, including, for example, processing by "double chamber" devices that collect (sense) and deliver (stimulate) signals both in the atrium and the ventricle, and "single chamber" devices that collect and deliver signals only in the atrium.

The location for detecting cardiac arrhythmia troubles to be processed by the invention, as will be discussed below, is not, however, limited to troubles detected in the atrium, and the invention will be able to be equally applied, mutatis mutandis, to the processing of trouble of the ventricular rhythm, the cavity of the myocardium then being considered as the ventricle, instead of the atrium.

The term "trouble of the atrial rhythm" or TdRA is a generic term that covers various atrial arrhythmia (episodes of non physiological acceleration of the rhythm) such as tachycardia, fibrillation, flutter, etc. These troubles or TdRA are all characterized at the detection, by a rapid atrial rhythm.

When one detects a TdRA, that is to say essentially when the atrial rhythm exceeds an admissible (selected or allowable) level, the pacemaker switches to operation in a mode called "desynchronisation" or "atrio-ventricular dissociation". In this mode, the ventricle is stimulated independently of the detected atrial rhythm, since this excessive rhythm is considered to be pathological.

In a general manner, one has observed that patients presented less atrial arrhythmia when they were always stimulated. A simple solution would be always to stimulate the atrium or atria at a fixed rhythm much greater than the physiological rhythm, but it would be nevertheless dangerous, in the long run, to the clinical state of the patient.

U.S. Pat. No. 4,419,996 describes a device susceptible to function according to two different modes, namely a first normal mode, inhibited, suitable to process bradycardia-type arrhythmias, and a second mode, dissociated, under the command of a programmed external device, in a manner as to treat the tachycardia-type arrhythmias.

The switching from the first to the second mode is obtained by bringing a magnet in proximity to the device, which supposes that it is the patient, or a therapist, that decides and controls the passage from one mode to the other. The device operates therefore in an non-automatic manner, and according to a personal appreciation of the patient or the therapist.

WO-A-95 09661 describes a device allowing the asynchronous stimulation of the atrium, stimulation that is implemented according to the evolution of the sinus rhythm of the patient and the information provided by a sensor of the activity of the patient, so as to adapt the functioning to real physiological needs of the patient. This device presents, however, the disadvantage of necessitating a supplementary information source (the sensor of activity) that, in addition, is not always available, for example, when the patient is at rest.

OBJECTS AND SUMMARY OF THE INVENTION

It is an object of the present invention to remedy the foregoing disadvantages by providing a device and method that insures a quasi-permanent stimulation of a cardiac cavity, especially of the atrial cavity, while preserving a rhythm that is adapted to physiological needs of the patient, that is to say, a rhythm very slightly greater than the underlying spontaneous (sinus) rhythm in the absence of stimulation, and doing so in an automatic and autonomous manner.

One aspect of the invention is directed to a device of the known type comprising:

means for detecting spontaneous electrical activity events in a cardiac cavity, preferably the atrium;

means for delivering a stimulation to the aforementioned cardiac cavity, controlled according to an actual escape interval so that, at each cardiac cycle, a stimulation is delivered to the cavity if no spontaneous event is detected at the end of a time corresponding to the end of the period of escape interval since the last spontaneous event or the last stimulation in the cavity;

means for counting the number of successive stimulated events; and means for discriminating between an extra-systole origin and a non extra-systole origin of the spontaneous events detected in the cavity.

According to the invention, the escape interval is modifiable at each cardiac cycle in a manner as to reduce by a first programmable value the actual escape interval after detection of a spontaneous event having a non extrasystole origin, and to increase the actual escape interval by a second programmable value after the deliver of a predetermined number of successive stimulations.

In one embodiment, the aforementioned predetermined number is 24; the first and/or the second programmable values are constant, and preferably the same, e.g., 47 ms. Alternatively, the first and/or the second programmable values can be variable, for example, a function of the average cardiac rhythm preceding the reduction of the escape interval. In addition, the escape interval can be limited, in the sense of the increase, to a maximal value corresponding to the base cardiac stimulation frequency programmed in the device; and the escape interval can be limited, in the sense of the reduction, to a minimal value corresponding to the maximal cardiac frequency authorized by the device, as such base and maximal rates may be predetermined or programmed.

BRIEF DESCRIPTION OF THE DRAWINGS

Further features, characteristics and advantages of the invention will appear to a person of ordinary skill in the art in view of the following detailed description of an example of implementation of the invention, made with reference to the drawings attached, in which.

DETAILED DESCRIPTION OF THE INVENTION

Figure 1:
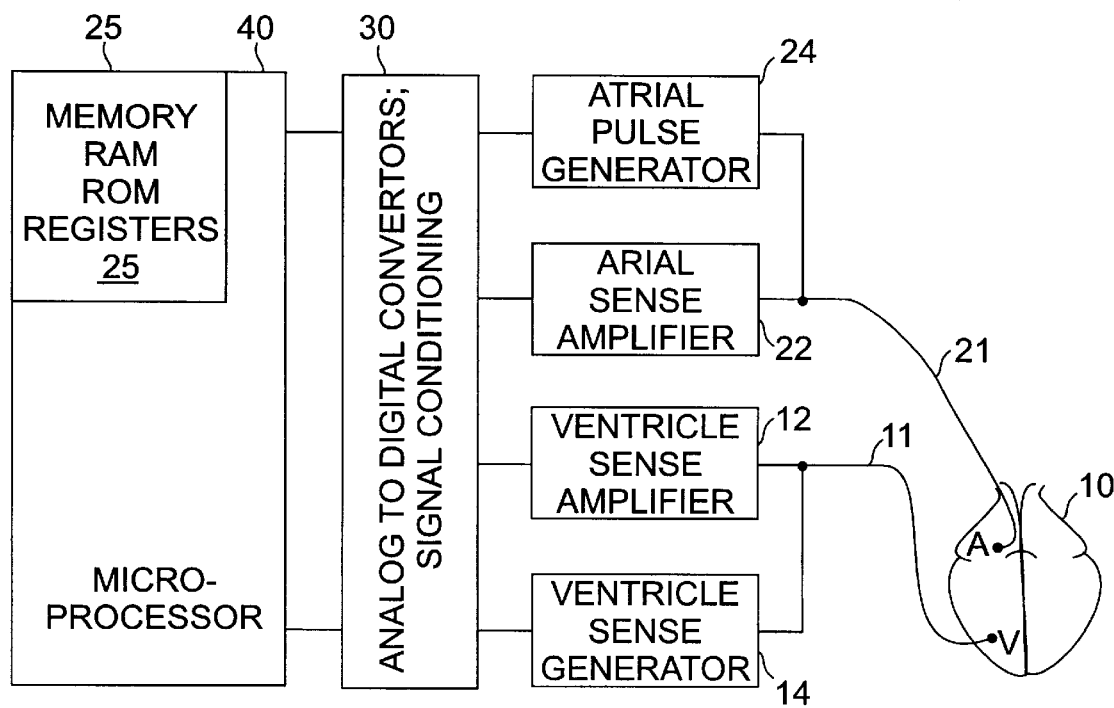
FIG. 1 is an schematic drawing of a device in accordance with the present invention.
Figure 2:
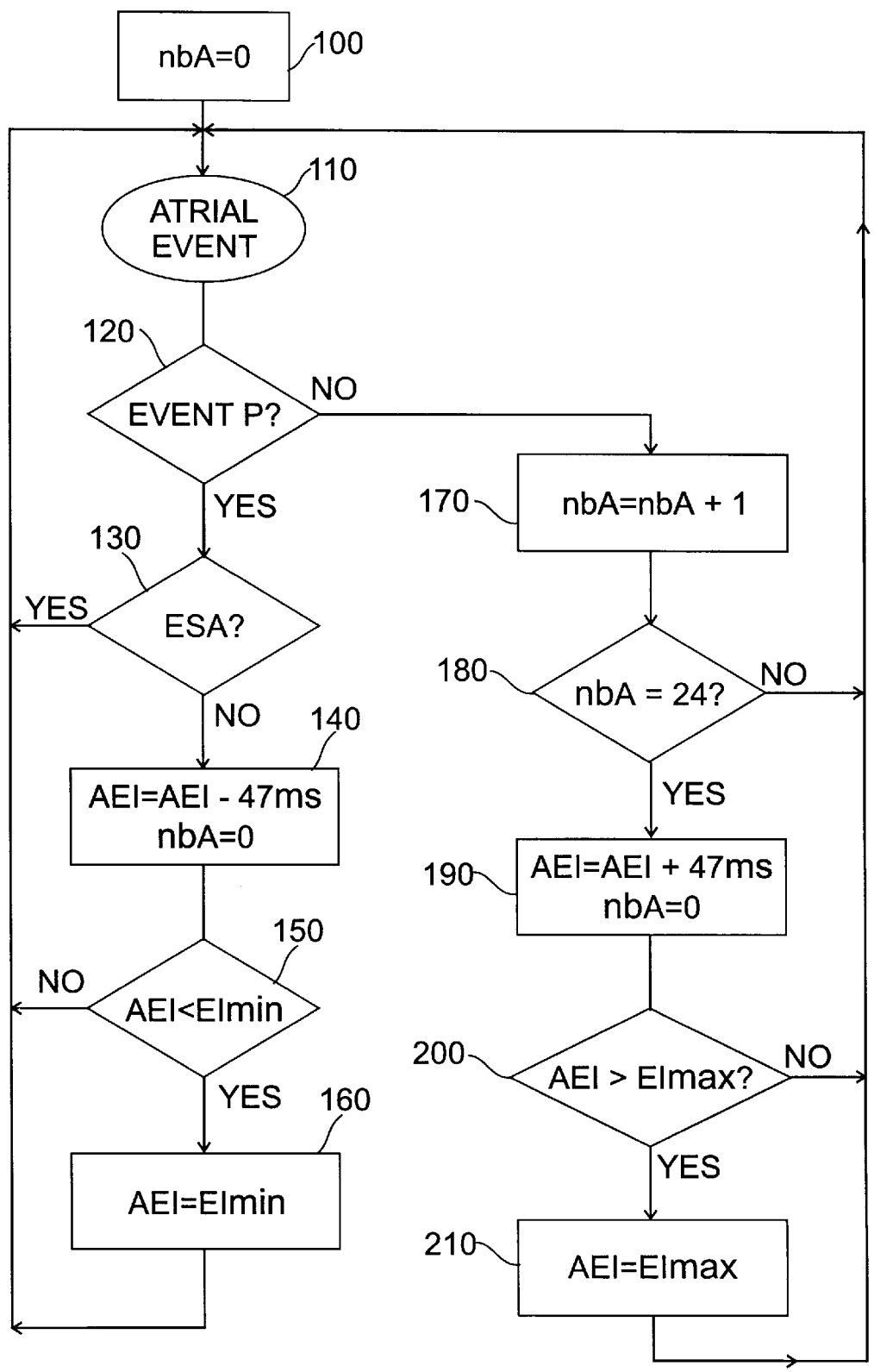
FIG. 2 is a flow chart illustrating an embodiment of the process of the present invention.

With reference to FIGS. 1 and 2, an embodiment will be described which is achievable, for example, by an appropriate programming of the software in a microprocessor-based pacemaker operating under software control.

The following definitions are used in the following description.

"P-Wave" or "event P": sensing of a spontaneous activity having its origin in the atrium.

"R-Wave" or "event R": sensing of a spontaneous activity having its origin in the ventricle.

"Event A": stimulation delivered to the atrium.

"Event V": stimulation delivered to the ventricle.

"Cardiac cycle": interval of time separating two events of a similar nature in the same cavity, for example separating two P-waves, or two events A.

"average PP": average interval of the atrial rhythm, calculated, for example, over 8 cardiac cycles not including an extrasystole.

"Escape interval" (EI): an interval of time, counted after a detection or a stimulation in a given cavity, to the end of which a stimulation is delivered to this same cavity if no spontaneous event has been detected in this same cavity. For the atrium, it concerns the atrial escape interval AEI.

"ESA": an atrial extrasystole. A P-wave is defined as an ESA if the interval of time separating this P-wave from the preceding atrial event is less than a given fraction of the average PP.

"ESV": ventricular extrasystole. One defines two types of ESV: an ESV of type 1 corresponds to a ventricular detection not preceded by an atrial event in a given time interval, for example, between 31 and 300 ms; an ESV of type 2 corresponds to a ventricular detection, preceded by an atrial event in an interval of time between 31 and 300 ms, but with a change of the time of conduction A–R in relation with the atrio-ventricular delay (AVD) of the preceding cardiac cycle: (AVD–AR>31 ms). For further details regarding the extrasystole, reference is made to EP-A-0 550 342 (and its corresponding U.S. Pat. No. 5,312,451 which is incorporated herein by reference), in the name of ELA Medical, the assignee hereof, which describes a detection and processing algorithm of ESV for an asynchronous stimulation of the atrium and a controlled stimulation of the ventricle.

The invention proposes to act continuously on the escape interval, especially the atrial escape interval (AEI) if one is interested in the atrial cavity, by adapting the value of this escape interval over the course of successive cardiac cycles, as a function of the intervening events during the course of these cycles.

More particularly, each time that one detects a spontaneous atrial event (P-wave) considered as sinusal and not as an ESA, one decreases the actual AEI interval by a first programmable value or a "slope of acceleration", typically 47 ms, for example. Then one applies this new interval to the current cycle.

Techniques allowing one to differentiate a normal sinusal activity from an ESA are in themselves known, for example, according to FR-A-2 544 989 and EP-A-0 488 840, (and its corresponding U.S. Pat. No. 5,226,415 the disclosure of which is incorporated herein by reference) all in the name of ELA Medical, the assignee hereof, that describe a mode of processing of ESA especially implemented in the model Chorus II 6234 dual chamber pacemaker of the same company.

After a given number of consecutive atrial stimulations (events A), for example, 24 consecutive stimulations, one lengthens the escape interval AEI by a second programmable value or a "slope of deceleration", being a typical value of 47 ms, for example. If one detects a P-wave that is considered by the device as being an ESA, one preserves the present value of the escape interval.

Thus, following one or more events of spontaneous and non extrasystole origin, one is going to accelerate the atrial stimulation frequency until this spontaneous rhythm disappears.

Conversely, after a predetermined number of consecutive stimulations, one is going to lengthen the escape interval until a spontaneous event is recovered, which allows one to stimulate the heart almost always at a rhythm slightly greater than the underlying spontaneous frequency of the patient, by taking account of physiological needs of the former. These cycles can include the extrasystole that are not taken in account and that do not interrupt the counting.

Of course, the excursion of the escape interval is preferably limited in the following two respects: regarding lengthening, the limit is the value of the interval corresponding to the programmed base frequency of the pacemaker, and regarding shortening, the limit is the value corresponding to the programmed maximal frequency of the pacemaker.

In another embodiment, instead of lengthening or shortening the interval by a fixed value each time that this interval is modified, one can lengthen it or shorten it by a value that is a function of the average of the cardiac rhythm preceding the modification of the escape interval, for example, a value that is a percentage of the preceding average cardiac period.

With reference to FIG. 2, an embodiment of the present invention is described. At step 100, the counter nbA is initialized and set equal to zero. On the detection of an atrial event at step 110, the event is tested at step 120 to determine if it is a P event or an A event. If it is a P event, it is tested at step 130 to determine if it is an ESA or not. If it is an ESA, than the routine returns to wait occurrence of another atrial event at step 110. If it is an ESA, then at step 140 the escape interval AEI is decreased by an amount, in this example 47 ms, and the counter nbA is set equal to zero. The thus adjusted AEI is then tested at step 150 to determine if the AEI has been reduced below the minimum escape interval EI min. If it was not, then the adjusted AEI is left unchanged, and if it was, then the adjusted AEI is set equal to EI min at step 160.

In the case that the test at step 120 reveals that the atrial event was not a P event, then the counter nbA is incremented by 1 at step 170. At step 180, the nbA count is compared to a limit of 24, and if nbA is less than 24, then the routine returns to wait for the next atrial event at step 110. If nbA is equal to 24, then the escape interval is incremented at step 190 by a limit, e.g., 47 ms, and the counter nbA is set to zero. Thereafter, the thus adjusted escape interval AEI is compared to a maximum limit EI max, and if it is greater, then the adjusted escape interval AEI is set equal to the limit EI max, and thereafter the routine returns to wait for the next atrial event at step 110.

Figure 3:
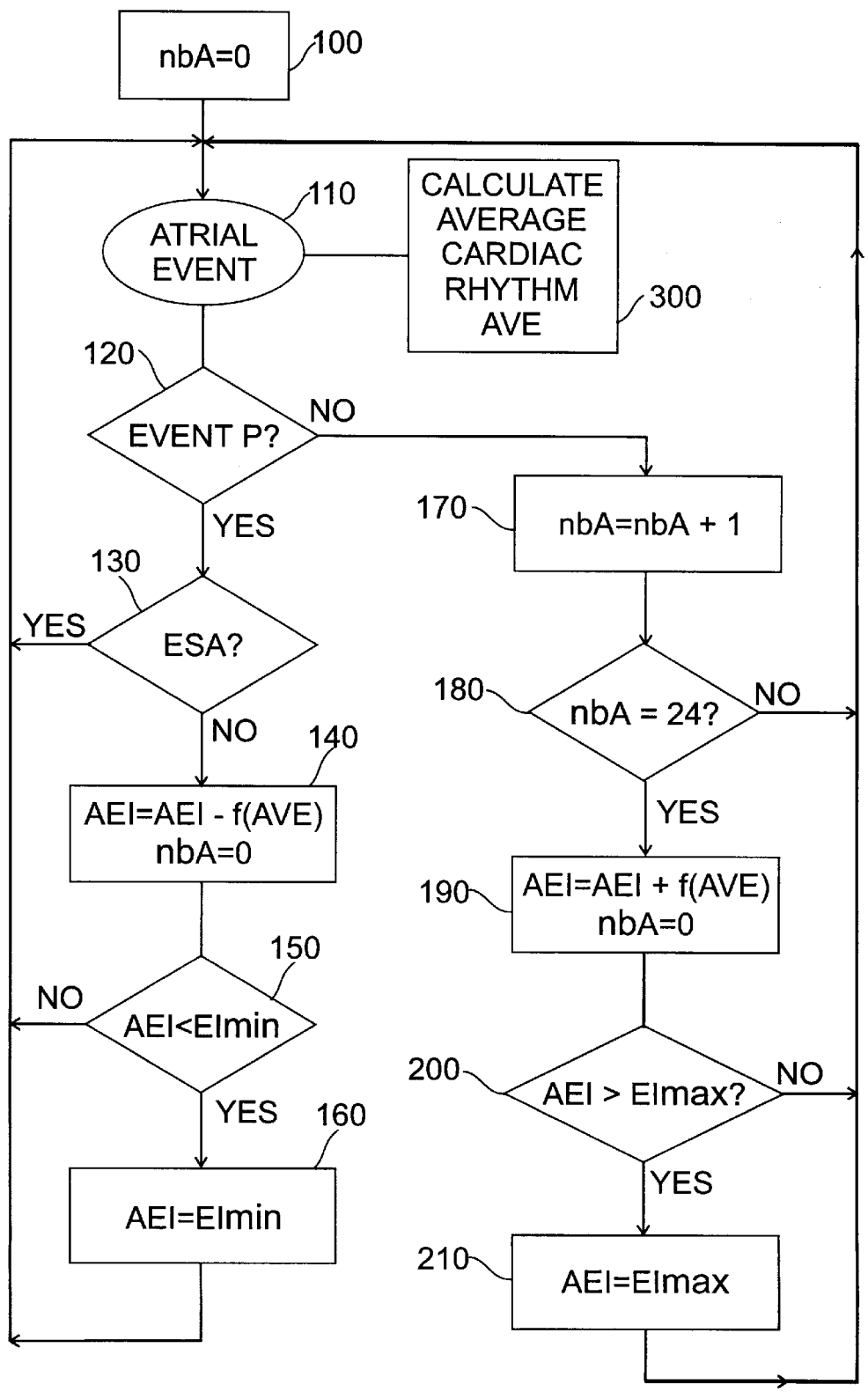
FIG. 3 is flow chart illustrating an alternate embodiment of the process of FIG. 2.

With reference to FIG. 3, an alternate embodiment of the embodiment described FIG. 2 is illustrated in which the similar aspects have the same reference claimants and which differs in the following respects. At step 300, the atrial event is detected and an average cardiac rhythm AVE is calculated. In this alternate embodiment, at step 140 the escape interval AEI is decreased by an amount that, in this example, is a function of the average cardiac rhythm (f(AVE)) and the counter nbA is set equal to zero. Similarly, if the atrial event is not a P event, then the escape interval is incremented at step 190 by a limit which, in this example, is a function of the calculated cardiac rhythm f(AVG), and the counter nbA is set to zero.

As would be understood by a person of ordinary skill in the art, the foregoing may be implemented in an active implantable medical device by use of discrete circuits (analog and/or digital circuits) or, alternatively, by a microprocessor based device operating under software control. Indeed, software suitable to perform the above described operations is believed to be easily written by and within the abilities of a person of ordinary skill in the art and may be stored in suitable memory, e.g., ROM, or in firmware.

As illustrated in FIG. 1, the detection of atrial and ventricular complexes and the measuring of the amplitude of these atrial and ventricular complexes are performed by conventional electronic means, e.g., digital microprocessor controlled devices having sense amplifiers, e.g., ventricle sense amplifier 12 and atrial sense amplifier 22 analog to digital conversion circuits 30 and microprocessor 40 with software 42 and suitable memory and registers 50 for data processing and manipulation. These devices also include an atrial pulse generator 24 and a ventricle pulse generator 14 for stimulating the atrium and ventricle under device control. The present invention is preferably implemented under software control, and occurs following acquisition of the cardiac electric signals by a conventional sense amplifier, e.g., by sensing electrical activity in the heart 10 atrium A and ventricle V using cardiac leads 11 and 21, preferably after the acquired signals have been conditioned and converted to digital form in the usual manner. Representative electronic circuits algorithm are those found in the series of dual chamber pacemakers, available from ELA Médical, Montrouge, France, offered under the CHORUS trademark. The method also used could be performed using, and the apparatus constructed of, discrete circuitry, if desired.

In addition, because the reduction of arrhythmia does not require any additional circuits (other than the conventional circuits for acquiring cardiac event information and conditioning those signals for processing by a microprocessor typically already existing in the device), software for processing such data in accordance with the present invention may advantageously be loaded into a RAM memory of microprocessor based device for use, for example, after the device without such processing capabilities has been implanted. Thus, software may be transferred by conventional telemetry into an already implanted device. Such conventional medical devices that might use of the invention are known and include, for example, the OPUS brand single chamber cardiac pacemaker, the Defender brand defibrillators, and the CHORUS brand dual chamber cardiac pacemakers, which are available from ELA Medical S.A., Montrouge, France, the assignee hereof.

One of ordinary skill in the art will appreciate that the invention can be practiced by embodiments other than those described herein, which one provided for purposes of illustration and not of limitation.

We claim:

1. An active implantable medical device comprising:
   means for detecting events of spontaneous electrical activity in a cardiac cavity;
   means for delivering a stimulation to said cardiac cavity, said means having an actual escape interval wherein said delivering means comprises means for delivering a stimulation to the cavity during a cardiac cycle if no spontaneous event is detected at the end of a time corresponding to the end of a period of said actual escape interval since the last detected spontaneous event or stimulation in said cavity;
   means for counting a predetermined number of successive stimulated events,
   means for discriminating between spontaneous events detected in the cavity of an extrasystole origin and a non-extrasystole origin, and
   means for modifying the actual escape interval at each cardiac cycle in a manner to reduce by a first programmable value the actual escape interval after detection of a spontaneous event of non-extrasystole origin, and to increase by a second programmable value the actual escape interval after delivery of a predetermined number of successive stimulations.

2. The device of claim 1, wherein the means for detecting further comprises means for detecting atrial cardiac events.

3. The device of claim 1, in which the first programmable value further comprises a function of the average cardiac rhythm preceding the reduction of the actual escape interval.

4. The device of claim 1, in which the second programmable value further comprises a function of the average cardiac rhythm preceding the increase of the escape interval.

5. The device of claim 1, further comprising means for limiting an increase of the actual escape interval to a maximal value corresponding to a programmed cardiac base frequency.

6. The device of claim 1, further comprising means for limiting a reduction of the actual escape interval to a minimal value corresponding to a maximal authorized cardiac frequency.

7. A method for reducing episodes of cardiac arrhythmia in an active implantable medical device comprising:
   detecting events of spontaneous electrical activity in a cardiac cavity;
   establishing an actual escape interval for delivery of a stimulation to the cardiac cavity if no spontaneous electrical activity is detected during said interval following a last detected spontaneous event or stimulation in said cavity;
   delivering a stimulation to the cardiac cavity, according to said actual escape interval, at each cardiac cycle, wherein delivering the stimulation further comprises delivering the stimulation to the cavity if no spontaneous event is detected at the end of a time corresponding to the end of a period of an actual escape interval since the last detected spontaneous event or stimulation in said cavity;
   counting a number of successive stimulated events;
   discriminating between spontaneous events detected in the cavity of an extrasystole origin or non-extrasystole origin; and
   modifying the actual escape interval at each cardiac cycle in a manner to reduce by a first programmable value the actual escape interval after detection of a spontaneous event of non-extrasystole origin, and to increase by a second programmable value the actual escape interval after delivery of a predetermined number of successive stimulations.

8. The method of claim 7, wherein the detecting step further comprises detecting atrial cardiac events.

9. The method of claim 7, further comprising providing 24 as the predetermined number.

10. The method of claim 7, further comprising providing the first programmable value as a constant.

11. The method of claim 7, further comprising providing the first programmable value as a function of the average cardiac rhythm preceding the reduction of the escape interval.

12. The method of claim 7, further comprising providing the second programmable value as a constant.

13. The method of claim 7, further comprising providing the second programmable value as a function the average cardiac rhythm preceding the increase of the escape interval.

14. The method of claim 7, further comprising limiting an increase of the escape interval to a maximal value corresponding to a programmed cardiac base frequency.

15. The method of claim 7, further comprising limiting a reduction of the escape interval to a minimal value corresponding to a maximal authorized cardiac frequency.

16. A cardiac pacemaker comprising a pulse generator, a cardiac event sense amplifier and a control means having a microprocessor and a control program for stimulating a cardiac cavity according to the method of claim 7.

17. An active implantable medical device comprising means for detecting events of spontaneous electrical activity in a cardiac cavity;

means for delivering a stimulation to said cardiac cavity, said means having an actual escape interval wherein said delivering means comprises means for delivering a stimulation to the cavity during a cardiac cycle if no spontaneous event is detected at the end of a time corresponding to the end of a period of said actual escape interval since the last detected spontaneous event or stimulation in said cavity;

means for counting at least twenty four successive stimulated events, means for discriminating between spontaneous events detected in the cavity of an extrasystole origin and a non-extrasystole origin, and means for modifying the actual escape interval at each cardiac cycle in a manner to reduce by a first programmable value the actual escape interval after detection of a spontaneous event of non-extrasystole origin, and to increase by a second programmable value the actual escape interval after delivery of said at least twenty-four successive stimulations.

18. An active implantable medical device comprising:

means for detecting events of spontaneous electrical activity in a cardiac cavity;

means for delivering a stimulation to said cardiac cavity, said means having an actual escape interval wherein said delivering means comprises means for delivering a stimulation to the cavity during a cardiac cycle if no spontaneous event is detected at the end of a time corresponding to the end of a period of said actual escape interval since the last detected spontaneous event or stimulation in said cavity;

means for counting a predetermined number of successive stimulated events, means for discriminating between spontaneous events detected in the cavity of an extrasystole origin and a non-extrasystole origin, and means for modifying the actual escape interval at each cardiac cycle in a manner to reduce by a constant value the actual escape interval after detection of a spontaneous event of non-extrasystole origin, and to increase by a second programmable value the actual escape interval after delivery of a predetermined number of successive stimulations.

19. An active implantable medical device comprising:

means for detecting events of spontaneous electrical activity in a cardiac cavity;

means for delivering a stimulation to said cardiac cavity, said means having an actual escape interval wherein said delivering means comprises means for delivering a stimulation to the cavity during a cardiac cycle if no spontaneous event is detected at the end of a time corresponding to the end of a period of said actual escape interval since the last detected spontaneous event or stimulation in said cavity;

means for counting a predetermined number of successive stimulated events, means for discriminating between spontaneous events detected in the cavity of an extrasystole origin and a non-extrasystole origin, and means for modifying the actual escape interval at each cardiac cycle in a manner to reduce by a first programmable value the actual escape interval after detection of a spontaneous event of non-extrasystole origin, and to increase by a constant value the actual escape interval after delivery of a predetermined number of successive stimulations.

* * * * *